United States Patent [19]

Lambson et al.

[11] 4,261,349
[45] Apr. 14, 1981

[54] SPINE IMMOBILIZATION APPARATUS

[76] Inventors: Robert A. Frosch, Administrator of the National Aeronautics and Space Administration, with respect to an invention of Kenneth H. Lambson, Salt Lake City, Utah; Hubert C. Vykukal, Los Altos, Calif.

[21] Appl. No.: 57,526

[22] Filed: Jul. 13, 1979

[51] Int. Cl.³ .............................................. A61F 5/04
[52] U.S. Cl. .................................................. 128/89 R
[58] Field of Search ................. 128/87 R, 89 R, 87 C, 128/88

[56] References Cited

U.S. PATENT DOCUMENTS

| 3,212,497 | 10/1965 | Dickinson | 128/87 R |
| 3,218,103 | 11/1965 | Boyce | 128/DIG. 20 |
| 3,745,998 | 7/1973 | Rose | 128/89 R |
| 3,762,404 | 10/1973 | Sakita | 128/DIG. 20 |

Primary Examiner—Robert W. Michell
Assistant Examiner—C. W. Shedd
Attorney, Agent, or Firm—Darrell G. Brekke; John R. Manning

[57] ABSTRACT

A spine immobilization method and apparatus are provided which make use of a normally flat, flexible bladder filled with beads or micro-balloons that form a rigid mass when the pressure within the bladder is decreased below ambient through the use of a suction pump so that the bladder can be conformed to the torso of the victim and provide the desired restraint. The bladder is strapped to the victim prior to being rigidified by an arrangement of straps which avoid the stomach area. The bladder is adapted to be secured to a rigid support, i.e., a rescue chair, so as to enable removal of a victim after the bladder has been made rigid. A double sealing connector is used to connect the bladder to the suction pump and a control valve is employed to vary the pressure within the bladder so as to soften and harden the bladder as desired.

2 Claims, 5 Drawing Figures

SPINE IMMOBILIZATION APPARATUS

CROSS REFERENCE TO RELATED APPLICATION

This application discloses subject matter in common with currently filed, copending application Ser. No. 057,465 entitled PRESSURE CONTROL VALVE.

FIELD OF THE INVENTION

The present invention relates to a method an apparatus for immobilizing the spine of a patient.

BACKGROUND OF THE INVENTION

Since the spinal cord is the connecting pathway for most mechanisms of the body's various organs, injury to it can cause dysfunction in almost all biological systems. Spinal cord injuries are calmitous, not only physically but psychosocially and financially. Approximately 10,000 to 12,000 new spinal cord injuries occur each year in the United States. In spite of advances in methods and appliances designed for the protection of the cord in spinal injuries, there are still too many patients able to move their extremities shortly after the accident who suffer irrepairable damage to the spinal cord through attempts that are made to move the patient from the scene of the accident to the hospital.

There are a number of techniques for the transport or removal of an accident victim suspected of having a spinal injury. For example, some of these techniques are described in *Fire Service First Aid Practices*, Fifth Edition, Oklahoma State University; Krueger et al., "Transportation and First Aid in Patients with Spinal Cord Injuries", New York State Journal of Medicine, Vol. 63, pp. 682-690, March 1963. In general, the techniques involve providing appropriate support for the body before any lifting takes place. An example of such a technique concerns the use of a spine board to which the victim is strapped (see the *Fire Services First Aid Practices* publication). Reference is also made to U.S. Pat. Nos. 4,034,748 (Winner) and 3,737,923 (Prolo).

As explained hereinbelow, the present invention utilizes a flexible bladder which is constructed so that it can be made rigid, and thereby conform to the shape of the victim, under the control of the user. In a specific embodiment, the bladder is filled with a plurality of so-called "microballoons" or spheres which form a rigid mass when the pressure within the bladder is less than ambient. A number of patents disclose devices of this type. One example is U.S. Pat. No. 3,212,497 (Dickinson) which discloses a moldable temporary splint comprising a flexible bag containing particles which consolidate into a rigid mass when the bag is evacuated. Two patents which employ this technique in restraining or immobilizing a patient are U.S. Pat. No. 3,762,404 (Sakita) and U.S. Pat. No. 3,745,998 (Rose). The Sakita patent discloses a "positioning aid" for immobilizing a part of the body of a medical patient which comprises an airtight bag filled with beads which form a rigid mass when the vacuum in the bag is destroyed by opening a self-closing valve. In certain embodiments, the bag is used to support the torso. The Rose patent discloses a somewhat similar vacuum-formed "support structure and immobilization device." A further patent of interest is U.S. Pat. No. 4,024,861 (Vincent) which discloses a spinal support in the form of an inflatable bag to which the victim is secured by straps so as to immobilize his spine during movement. Reference is also made to U.S. Pat. No. 3,415,243 (Sheldon) which discloses a surgical cast that includes a plurality of reagents which are reactive when intermixed to form a hardenable cast material and which are imbedded in surgical gauze. Rupture of an encapsulation for one of the reagents enables mixing of the reagents.

SUMMARY OF THE INVENTION

As was discussed briefly hereinabove, in accordance with the present invention, a spine immobilization method and apparatus are provided which makes use of rigidifiable bladder construction which is broadly similar to those described previously. The bladder construction is specifically adapted for use in immobilizing the spine of an accident victim and, as will become apparent, possesses a number of advantages over the general purpose support or immobilization devices of the prior art. The method and apparatus of the invention enable the spine of such an accident victim to be immobilized and restrained from movement in a very rapid, efficient manner and permit the victim to be safely removed from the accident scene in an extremely short time after help arrives.

According to a preferred embodiment thereof, the spine immobilization apparatus of the invention comprises a normally flat, flexible bladder including means contained therein (such as the microballoons referred to above) for causing the bladder to become rigid in response to a change in the internal pressure within the bladder. The bladder includes a head portion and a body portion adapted to conform to the head and torso of a patient whose spine is to be immobilized. The spine of the wearer is immobilized when the bladder becomes rigid. The apparatus also includes an inlet/outlet device for connecting the interior of said bladder to a pressure source, preferably in the form of a vacuum pump, as well as a securing or positioning arrangement for securing said bladder in position on the patient and for assisting in securing said bladder to a rigid support for enabling the patient to be transported.

The securing arrangement preferably comprises a first pair of straps which cross one another over the chest of the patient above the stomach region and a further pair of straps which engage a lower portion of the torso beneath the stomach region, so that the stomach region is kept free of any restraining forces. This is important in that the stomach muscles are required in breathing under these circumstances and any restraint on the stomach and hence on breathing could be detrimental to the health of the patient. Advantageously, a forehead strap arrangement and a chin strap arrangement are also provided, the forehead strap arrangement comprising a pair of straps one of which includes a hook pile fastener and the other of which includes a loop pile fastener, thereby enabling ready connection and disconnection.

The rigid support preferably comprises a conventional collapsible rescue chair and the securing arrangement of the apparatus also comprises a plurality of straps for securing the bladder to the chair.

The flexible bladder further comprises filter means for filtering air passing into the bladder and for preventing the microballoons contained in the bladder from escaping from the bladder. As noted, the pressure source preferably comprises a vacuum pump which produces a subatmospheric pressure within the bladder; the apparatus also includes a suitable connection means e.g., a connecting line formed from rubber tubing, for connecting the bladder to the pump as well as a self-sealing connector between the bladder and pump for retaining the negative pressure within the bladder when the connection to the vacuum pump is broken by disconnecting the connector. A control valve disposed in the connecting line controls the air admitted into and released from bladder so as to control rigidification, i.e., hardening and softening of the bladder.

In the use of the bladder in removing an accident victim having a possible spinal injury from the accident scene, the bladder is applied to the back of the torso of the victim so as to conform the shape of the bladder to the shape of the torso of the victim; suction is applied to the bladder to rigidify the bladder and to thereby immobilize the spine, the rigidified bladder is then secured to a rigid support which permits the victim to be transported; and the victim is thereafter transported from the accident scene using the rigid support.

The step of conforming of the shape of the bladder to the shape of the torso of the victim preferably includes an intermediate step of reducing the suction applied to the bladder so as to soften the bladder when the latter has been previously rigidified to thereby permit the bladder to be more closely fit to the shape of the torso of the victim. Filler material, formed, e.g., by blankets rolled to form wedges, is inserted in the space which exists between the bladder and the rigid support in the area of the back.

Other features and advantages of the present invention are set forth in or apparent from the detailed description of a preferred embodiment of the invention found hereinbelow.

DESCRIPTION OF A PREFERRED EMBODIMENT

Figure 1:
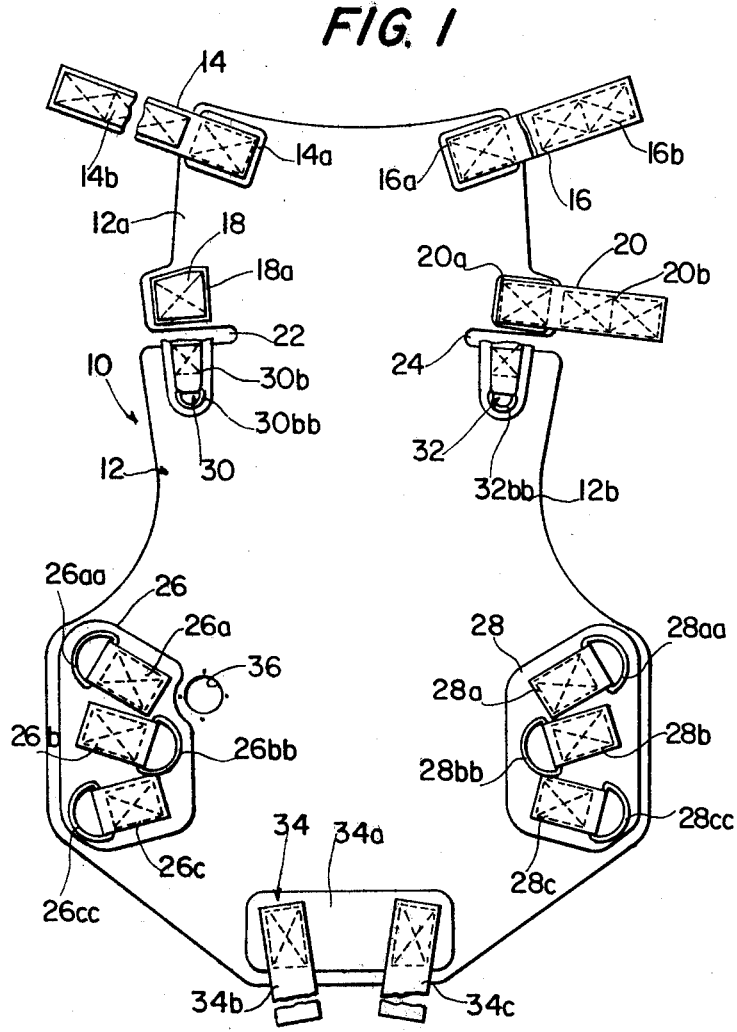
FIG. 1 is a plan view of a bladder and strapping assembly constructed in accordance with a preferred embodiment of the invention.

Referring to FIG. 1, there is shown a plan view of the back side of the bladder and strapping assembly of the spine immobilization apparatus of the present invention. The bladder and strapping assembly, which is generally denoted 10, includes a flat bladder portion or bladder 12 which is preferably fabricated of a tough, flexible, resilient airtight material. Suitable plastic materials are manufactured by Stevens Elastomeric and Plastic Products, Inc., Easthampton, Mass., under the trade name of Urethane Film. A first Urethane Film includes urethane and a polyester whereas a second Urethane Film includes urethane and a polyether. Also, bladder 12 may comprise a fabric coated with an elastomeric material such as neoprene.

The bladder 12 includes a head portion 12a to which is attached a first pair of straps or webbings 14 and 16 which serve as forehead straps. Strap 14 is attached, such as by sewing, to a doubler 14a which is bonded to the bladder 12. Strap 14 has secured thereto one half of a releasable fastener such as a well-known "Velcro" fastener comprising releasably interlocking loop and hook piles. In the exemplary embodiment under consideration, a loop pile 14b is attached to the near face of strap 14. Similarly, strap 16 is attached to a doubler 16a and has a hook pile secured to the far (non-illustrated) face thereof. A further loop pile 18 is attached to a doubler 18a bonded to head portion 12a of bladder 12 so as to face forwardly or outwardly from the plane of the drawing below strap 14 and a further hook pile 20b is attached to the far side of a further strap 20 secured to a further doubler 20a bonded to bladder 12. Strap 20 constitutes a chin strap for the bladder 12.

A pair of slots 22 and 24 located between the head portion 12a of bladder 12 and a body portion 12b permit separate folding of the sides of the head portion 12a around the head of a victim.

The body portion 12b of bladder 12 includes a further pair of doublers 25 and 28 bonded thereto. Doubler 26 has three webbing anchors 26a, 26b and 26c sewn thereto, three steel D-rings, respectively denoted 26aa, 26bb, 26cc being attached to individual ones of the anchors, as illustrated. Similarly, doubler 28 has three webbing anchors 28a, 28b and 28c sewn thereto, with D-rings 28aa, 28bb and 28cc attached to these anchors.

Figure 2:
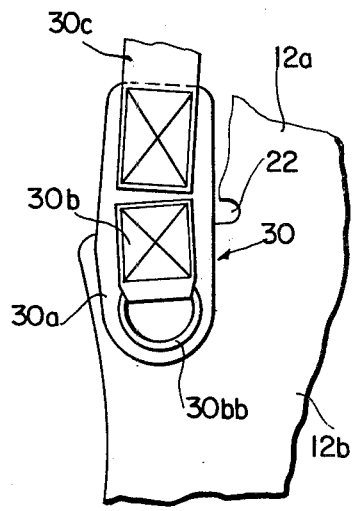
FIG. 2 is a plan view of a detail of the assembly shown in FIG. 1.

A further pair of strap or webbing assemblies 30 and 32 are secured to the top of body portion 12b adjacent to the slots 22 and 24, respectively. The strap assemblies 30 and 32 are substantially indentical and need not be described separately. Thus, as shown in FIG. 2, strap assembly 30 comprises a doubler 30a to which is attached a webbing anchor 30b which carries a pair of D-rings, only one of which, denoted 30bb, is shown. An elongate strap 30c is sewn to doubler 30a. In the partial showing of strap assembly 32 in FIG. 1, a corresponding webbing anchor 32b and D-ring 32bb are illustrated.

A further strap or webbing assembly 34 is located at the bottom of bladder 12. Strap assembly 34 comprises a doubler 32a having a pair of straps 34c and 34d sewn thereto.

An aperture 36 located in bladder 12 adjacent to doubler 26 cooperates with a filter assembly (not shown in FIG. 1) to provide deflation of bladder 12 in a manner described below in connection with FIG. 3.

Before considering the bladder deflation system shown in FIG. 3, reference will be made to FIG. 4 where the flat bladder of FIGS. 1 and 2 is shown in the operative position thereof, i.e., as attached to an accident victim. As illustrated, the head portion 12a wraps around the head of the victim with straps 14 and 16 being secured together by the "Velcro" fasteners around the forehead and strap 20 connected to "Velcro" pile 18 beneath the chin. Strap 30c of strap assembly 30 extends diagonally across the chest and is secured to the D-ring 28aa of upper webbing anchor 28a while strap 32c extends diagonally across the chest in the opposite direction and is secured to the D-ring 26aa of the other upper webbing anchor 26a. Similarly, strap 34c extends from the rear of bladder 12 between the legs of the victim and is secured to D-ring 26cc of lower webbing anchor 26c while strap 34b also extends between the legs of the victim and is secured to the D-ring 28cc of the other lower webbing anchor 28c. It is important to note that the upper and lower straps 30c, 32c, and 34b, 34c do not enage the stomach region of the patient because an individual with a spinal injury utilizes the stomach muscles to breath and thus any restrictions in this region should be avoided.

Figure 3:
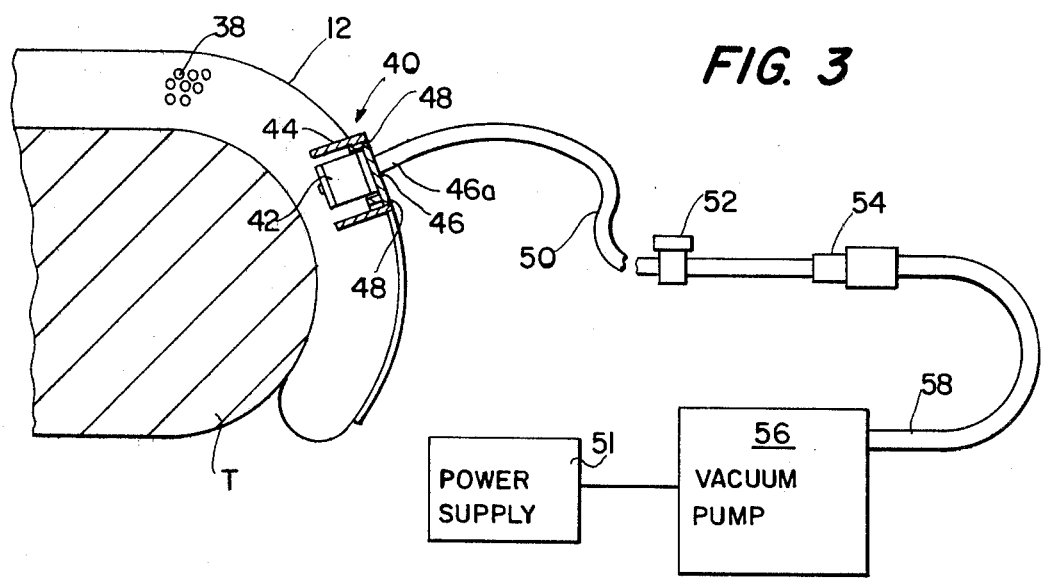
FIG. 3 is a schematic diagram, partially in cross section, of the bladder assembly and associated suction apparatus, in use.
Figure 5:
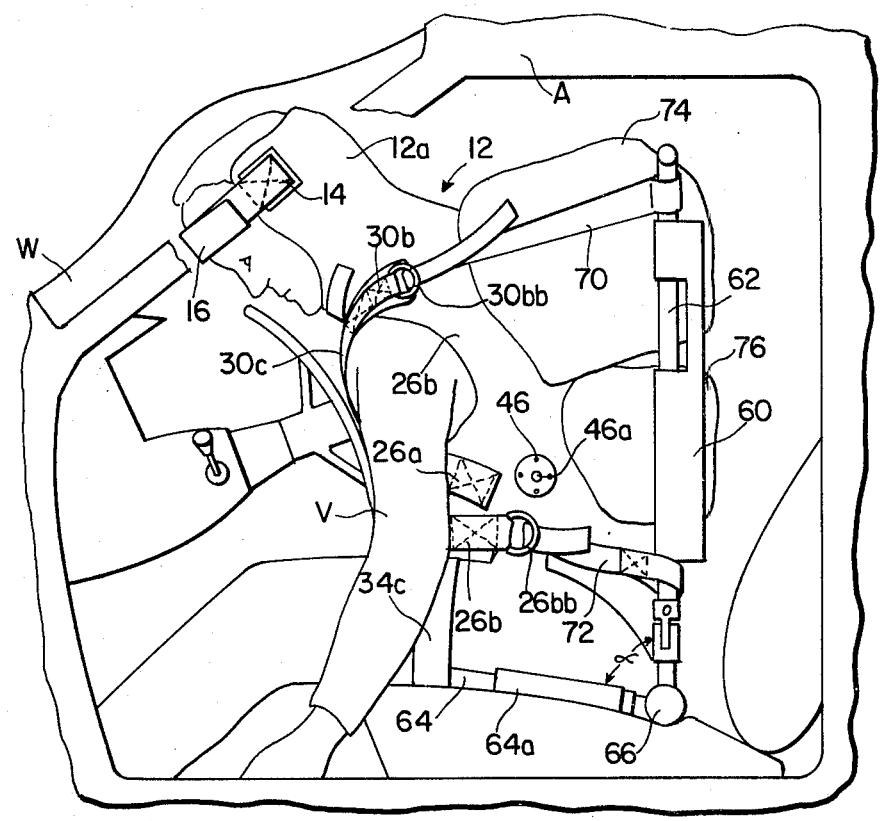
FIG. 5 is a side view of the bladder assembly of the invention in use in combination with an associated support arrangement, with an accident victim seated behind the steering wheel of an automobile.
Figure 4:
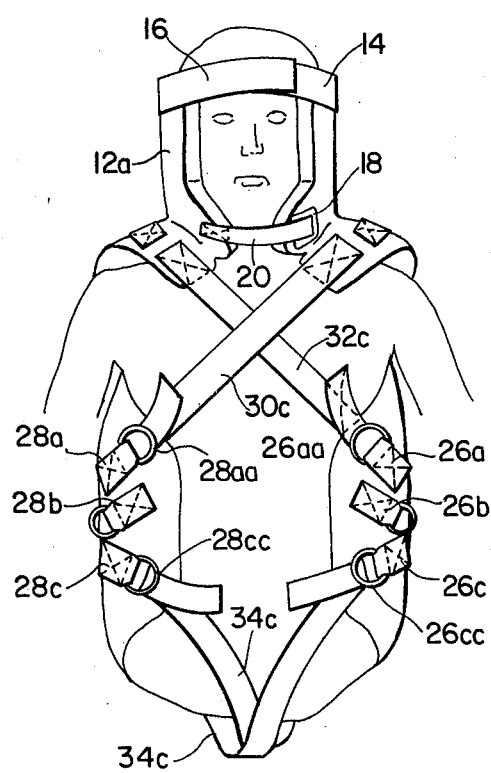
FIG. 4 is a front view of the bladder assembly of the invention in use on a patient.

Referring to FIG. 3, the bladder assembly of the present invention is shown in the "inflated" state thereof. FIG. 3 is a highly diagrammatic view with the straps omitted and the torso of the victim, denoted T, facing towards the bottom of the drawing. As explained hereinabove, the bladder 12 is filled with very fine microballoons (not specifically shown but indicated schematically at 38). Suitable microballoons are sold by Emerson & Cuming, Inc., Canton, Mass. The "hydrospace" grade microballoon is preferred because of its resistance to moisture absorption. When air is withdrawn from the bladder 12, the microballoons form a rigid, concrete-like mass. In FIG. 3, a portion of the microballoon filled bladder 12 is shown in engagement with the torso T of the accident victim. A filter unit 40 mounted in opening 36 (FIG. 1) in the bladder 12 includes a filter 42, a filter protector ring or annulus 44 having a plurality of equispaced holes in the wall thereof and a circular disc-like filter adapter plate 46. Filter 42 may comprise a Toyota fuel filter No. RE-165. Adapter plate 46 is connected to screws 48 to protector ring 44 and plate 46 includes an inlet nipple 46a adapted to be attached to a length of tubing or hose 50 through which suction is applied. An adjustment valve 52 is included in the connection tubing 50 which provides a controlled amount of inlet air so as to permit variation of the evacuation rate. In this way, a paramedic can reversibly soften and harden the microballoons 38 which are contained within the bladder 12 and thereby soften and harden the "conformal blanket" formed by the bladder 12 so as to best fit the patient. A conventional quick-disconnect coupling 54 is employed which is of the type that will provide double shut-off to maintain the vacuum on both sides of the coupling 54 and thus valve 52 is also used to provide inlet air so as to soften bladder 12 when the latter has been made rigid due to prior vacuum pumping. The valve 52 is the subject of commonly assigned, concurrent filed patent application Ser. No. 057,465, entitled PRESSURE CONTROL VALVE.

A conventional vacuum pump 56, powered by power supply 51, is connected to the socket of coupling 54 through a further length of tubing 58. A 12-volt d.c. pump is preferred. A power supply for such a pump is readily available on ambulances or fire trucks. Where 115VAC, 60 Hz power supply is available, pump 56 may be a diagram vacuum pump Model 2017 CA18 manufactured by Thomas Industries of Sheboygan, Wis.

Referring to FIG. 6, the use of the spine immobilization apparatus of the invention is illustrated. As shown in FIG. 6, an accident victim V is viewed through the doorway of a sub-compact car A and is slumped over the wheel with his head rammed into the windshield W. The position of the victim illustrated is, of course, typical for many types of collisions. Today there are many tools commercially available that are suited for accident rescue use that enable an operator to quickly cut or burn through an accident vehicle skin and remove sections that impede rescue of a vehicle occupant. The bladder assembly of the invention is used in connection with an articulated rescue chair 60. The rescue chair may be a "Ferno-Washington" No. EM5-585-4357 which is manufactured under one or more of the following patents: U.S. Pat. Nos. 3,122,758; 3,057,655; 3,289,219; 3,637,232; 3,684,307; 3,088,770; 2,877,047; 3,498,698; 2,747,919; 2,958,873; 2,841,438; 3,380,085; 3,644,944; and 3,752,527. It will thus be understood that the rescue chair 60 is a commercially available device and the construction thereof forms no part of the present invention. The rescue chair 60 comprises four snap together pieces, viz. two back pieces and two buttocks pieces, which form the back support portion 62 and buttocks support portion 64. The latter includes a small metal buttocks support plate 64a. The angle α between the back portion 62 buttocks support portion and 64 can be adjusted and a knob 66 locks the angle chosen.

In order to immobilize the spine of the victim V, bladder assembly 10 is slipped behind his back and the straps 14, 16, 20, 30c and 32c are engaged as described above in connection with FIG. 4 so that straps 14 and 16 are closed together at the forehead, strap 20 is engaged with fastener 18 beneath the chin and straps 30c and 30d criss-cross over the chest. Vacuum pump 56 is then connected to the filter assembly 40 including filter support plate 46 so that a vacuum can be applied to the microballoons 38 within bladder 12. As the air is withdrawn from bladder 12 through inlet/outlet 46a, the microballoons 38 form a rigid, concrete-like mass as described hereinabove. As also was mentioned, valve 52 can be used to control the entry and outgo of air so that the bladder can be softened in order to best fit the same to the torso of the victim.

After the spine of the victim has been immobilized, the bladder assembly 10 is attached to the rescue chair 60. The bladder assembly is connected to the rescue chair 60 by means of a pair of straps or webbings 70 (one of which is shown) which attach to each side of an upper portion of the back portion 62 of chair 60 and to the D-rings 30bb and 32bb of the bladder assembly 12, one such strap 70 being visible in FIG. 6. In addition, a further pair of straps 72 (one of which is shown) connect D-rings 28bb and 26bb to a lower part of the back portion 62 of rescue chair 60. Loose webbing straps 34b and 34c form a lap belt suitable to the victim. The rescue chair 60 is slipped into position with as little movement of the patient as possible, although it will be appreciated that the use of bladder assembly 10 greatly decreases the risk of movement by immobilizing the spine. In order to fill the space between the back of the victim V and the back portion 62 of chair 60, a pair of simple cloth wedges 74 and 76 are inserted in this space. These wedges are preferably formed by blankets or the like which are compactly rolled to achieve the wedge shape. With the wedges 74, 76 in place and all straps suitably adjusted, the victim can be removed from the automobile through prescribed manipulation of the rescue chair 60.

Although the invention has been described in detail with respect to an exemplary embodiment thereof, it will be understood by those of ordinary skill in the art that variations and modifications may be effected within the scope and spirit of the invention.

What is claimed is:

1. Apparatus for immobilizing the spine of an accident victim before removing said victim from the accident site and for use with an air evacuator and an articulated rescue chair, said apparatus comprising:

a normally flat flexible bladder having solid discrete particle means contained therein for causing said bladder to become rigid when the air within said bladder is withdrawn, means for connecting the interior of said bladder to said air evacuator;

said bladder having a head portion and a torso portion, said head portion adapted to cover the back and side areas of the victim's head and neck, said torso portion having first and second lateral regions and a back region further including a base region, said shoulder, lateral and back regions adapted to cover the shoulders, sides and back of the torso of said victim, respectively, without restricting motion of the victim's arms or stomach, said base region being at an end of said bladder opposite said head portion and in proximity to said victim's buttocks;

means for securing said torso portion of said bladder to said victim, said securing means including a first strap extending from said first shoulder region to said second lateral region, a second strap extending from second shoulder region to said first lateral region whereby said first and second straps cross one another over the chest of said victim, a third strap extending from said first lateral region through the crotch of the victim to said base region, and a fourth strap extending from said second lateral region through the crotch of said victim to said base region whereby said third and fourth straps skirt the stomach region of said victim;

means for fastening said head portion of said bladder to said victim, said fastening means including a forehead strap and a chin strap; and anchors located at both shoulder regions and both lateral regions adapted to secure said bladder to said articulated rescue chair whereby said accident victim may be removed from the accident site by gripping said chair.

2. Apparatus as set forth in claim 1 wherein a connecting line couples said air evacuator to said connecting means and a control valve means is disposed in said connecting line for controllably admitting air at atmospheric pressure into said bladder while the interior of said bladder is still coupled to said air evacuator so as to control rigidification of said bladder.

* * * * *